Figure 1:
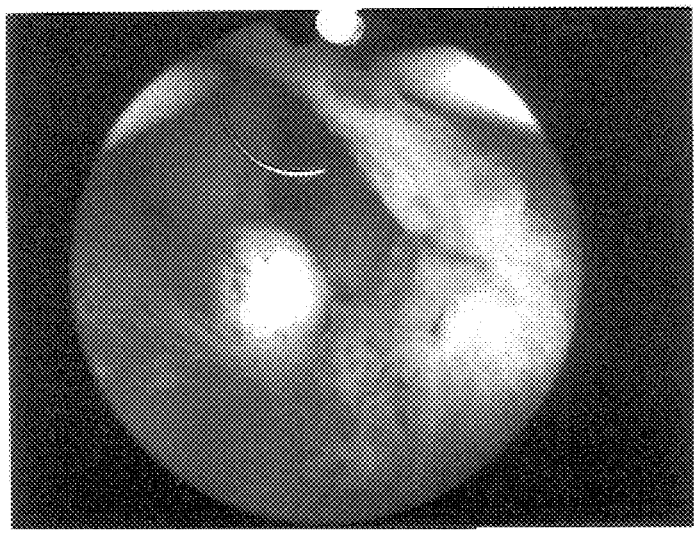

United States Patent [19]
Engel et al.

[11] Patent Number: 6,106,805
[45] Date of Patent: Aug. 22, 2000

[54] DIAGNOSTIC COMPOSITION CONTAINING AN LH-RH ANTAGONIST FOR HYSTEROSCOPY

[75] Inventors: Jürgen Engel, Alzenau; Klaus Diedrich, Gross-Sarau; Ricardo Felberbaum, Lübeck, all of Germany

[73] Assignee: Asta Medica Aktiengesellschaft, Germany

[21] Appl. No.: 08/961,085

[22] Filed: Oct. 30, 1997

[30] Foreign Application Priority Data

Oct. 30, 1996 [DE] Germany ............... 196 44 994

[51] Int. Cl.⁷ .................. A61K 49/00; A61K 38/04; A61K 38/00; G01N 1/00
[52] U.S. Cl. .................. 424/9.1; 424/9.5; 530/313; 530/328; 514/15; 514/800; 930/130
[58] Field of Search .................. 424/9.1, 9.5, 9.51, 424/9.52; 530/313, 328; 514/15, 800, 14; 930/130

[56] References Cited

U.S. PATENT DOCUMENTS

| | | |
|---|---|---|
| 4,800,191 | 1/1989 | Schally et al. ............... 514/15 |
| 5,198,533 | 3/1993 | Schally et al. ............... 530/313 |
| 5,574,011 | 11/1996 | Tien ............... 514/14 |
| 5,663,145 | 9/1997 | Engel et al. ............... 514/15 |

OTHER PUBLICATIONS

Ph. Merviel, J. L. Mergui, J. Salat–Baroux, Operative–Hysteroscopy in 1995. Equipment, technique, indications and results. Contracept. Fertil. Sex.—1995—vol. 23, n 9, pp. 516–523.

L. Boubli, B. Blanc, B. Barry, E. Bautrant, Treatment by LHRH agonist before Hysteroscopic resection of myoma, Contracept. Fertil. Sex.—1992—vol. 20, n 5, pp. 567–570.

*Primary Examiner*—Jose' G. Dees
*Assistant Examiner*—Michael G. Hartley
*Attorney, Agent, or Firm*—Cushman Darby & Cushman

[57] ABSTRACT

The invention relates to a diagnostic composition for improving the effectiveness of hysteroscopy, characterized in that it contains an LH-RH antagonist, in particular cetrorelix. The composition is envisaged for use prior to hysteroscopy and/or for preparation for surgery, specifically in a single dose of between 0.1 and 2 mg/kg.

However, the composition can also be administered, for use prior to hysteroscopy and/or for preparation for surgery, in a multiple dose of between 0.01 and 0.5 mg/kg, preferably spread over 1–14 days. The composition is furthermore suitable for use in hysteroscopy in combination with the subsequent treatment of pathological conditions of the uterus such as myoma and endometrial hyperplasia.

5 Claims, 1 Drawing Sheet

(1 of 1 Drawing Sheet(s) Filed in Color)

DIAGNOSTIC COMPOSITION CONTAINING AN LH-RH ANTAGONIST FOR HYSTEROSCOPY

The invention relates to a diagnostic composition to be used, in particular, in preparing for hysteroscopy. Hysteroscopy is to be understood as being the endoscopic inspection of the uterine cavity using a special endoscope (hysteroscope). Hysteroscopy is an essential diagnostic method for assessing various uterine diseases, for example myomas and endometrial hyperplasia.

It is known from Gynaecol.-Endoscopy 4:4 259–264 1995 to employ GnRH analogues, in this case triptorelin, prior to laparoscopic myomectomy. Furthermore, endometrial hyperplasia has been treated with the LH-RH agonist tryptorelin in association with hysteroscopic and diagnostic curettage (Contraception-Fertilite-Sexualite 23, 9, 516–523, (1995)). It is known from J. Gynaecol. Surg., 11:2, 65–70 (1995) to assess the effect of endometrial thinning with Gn-RH agonists (Zoladex) with regard to the results of hysteroscopic, endometrial electrosurgical resection. It is recommended that the endometrium be prepared prior to hysteroscopic surgery.

Results obtained in association with the treatment of infertility with GnRH analogues are known from TW. Gynaecol. 6:6,382–390 (1993), according to which [lacuna] the volume of leiomyomas is effected prior to laparoscopic myomectomy or hysteroscopic resection.

It has not previously been known to use LHRH antagonists, in particular cetrorelix, in connection wish hysteroscopic diagnosis or preparation for surgery.

The object of the invention is therefore to provide a composition for improving the results of hysteroscopy carried out in connection with the diagnosis of uterine conditions, in particular in association with endometrial hyperplasia, leiomyomas or malignant diseases. The invention additionally makes it possible to carry out non-invasive therapy or an operation without any long preparation time. This can simultaneously be combined with a treatment of the abovementioned diseases.

The object is achieved by employing LH-RH antagonists, in particular the LH-RH antagonist cetrorelix, which is known, for example, from EP 0 299 402, in preparing for hysteroscopy in association with the abovementioned applications.

Because the effect of cetrorelix begins immediately, the use of this compound is also particularly indicated in connection with the diagnosis and therapy of myoma bleeding, for example.

Diagnosis can advantageously move on directly into therapy using therapeutic doses.

Leiomyomas, for example, can be treated in accordance with the following scheme:

EXAMPLE

In one embodiment of the invention, from 0.1 to 2 mg of cetrorelix per kg of body weight are injected as a single dose or in amounts of from 0.01 to 0.5 mg per kg of body weight which are spread out over 1 to 14 days. This results in a decrease in the thickness of the endometrial layer and, consequentially, in the possibility of more effective hysteroscopic assessment and therapy of pathological conditions. Due to the fact that the effect of cetrorelix begins rapidly, administration of this compound is also particularly indicated in association with the diagnostic preparation for operations, such as for mammary carcinomas, which cannot be delayed.

Table 1 below shows the decrease, or the stagnation, in endometrial growth as monitored in a female patient having the initials 112 KB, and is explained in that which follows: Cetrorelix Pamoate: Provisional Results of the Clinical Experiments Treatment of a female patient with uterine fibrosis, which was operated on. Injection of 60 mg of cetrorelix on days 2 and 28 of the menstrual cycle.

The endometrium was measured by ultrasonics and did not exhibit any growth during the treatment with cetrorelix. Hysteroscopic and laparoscopic myoma resection was carried out with ease and without any significant blood loss only 2 months after beginning the cetrorelix therapy.

Due to the fact that the thickness of the endometrial layer begins to decrease immediately after injecting cetrorelix, a short period, of from 7 to 14 days, of treatment with cetrorelix is sufficient for diagnostic investigations or for ablation of the endometrium.

TABLE 1

| Patient | Dose | Date | Treatment days | Endometrium Time [mm] | E2 pg/ml | Comments |
|---|---|---|---|---|---|---|
| 11 KB | | 26.02.96 | screening | flat/even | | |
| " | 1st injection 60 mg of cetrorelix pamoate | 03.03.96 | Day 0 | 10:15 | 25 | |
| " | | 11.03.96 | Day 7 | 16:40 2 | <5 | |
| " | | 08.03.96 | Day 14 | 17:30 flat/even | 17 | |
| " | | 25.03.96 | Day 21 | — 3.1 | 40 | |
| " | 2nd injection 60 mg of cetrorelix pamoate | 01.04.96 | Day 28 | 18:00 flat/even | 88 | |
| " | | 15.04.96 | Day 42 | 17:00 flat/even | 25 | |
| " | | 29.04.96 | Day 55 End of the study | 16:15 flat/even | 73 | |
| " | | 07.05.96 | Day of operation | 14:00 | 114 | laparoscopic myoma enucleation hysteroscopic myoma resection |

Figure 3:
Figure 2:
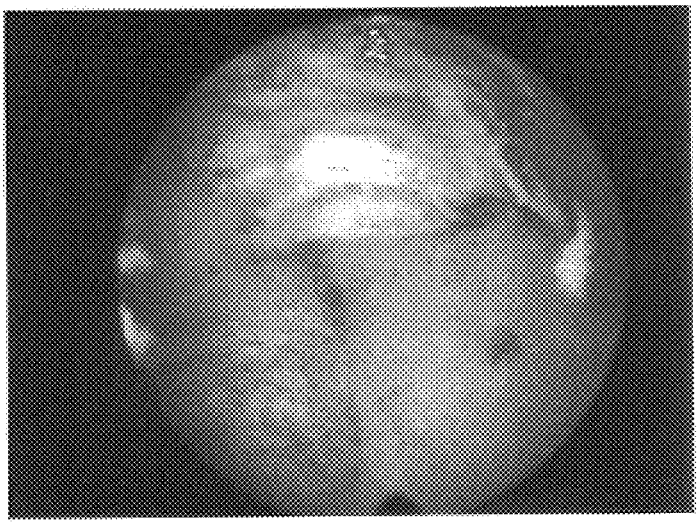

Explanation of Enclosed FIGS. 1 to 3

The file of this patent contains color drawings. Copies of this patent with color drawings will be provided by the Patent and Trademark Office upon request and payment of the necessary fee.

FIG. 1 shows a surgical photograph before beginning hysteroscopic myoma ablation FIG. 2 shows a surgical photograph following hysteroscopic myoma ablation.

Ostium pubae internum at the top on the left

FIG. 3 shows the enucleation of the subserosal fundus myoma

The principal advantages of the invention are:

→improved diagnostic principle based on rapid hormone suppression and consequently rapid reduction or interruption of the endometrial volume and consequently improvement in hysteroscopic diagnosis and shorter period of treatment as compared with known methods →very good tolerability due to the absence of initial stimulation (flare up).

Particular Advantages of Premedication with Cetrorelix are

→it is possible to begin treatment irrespective of menstrual cycle status

→short treatment period of from 7 to 10 days and therefore no side effects and no, or only trivial, symptoms of hormone deficiency →good timing for the hysteroscopic inspection Comparison with Existing Therapies →LHRH agonists: initial flare up a) long period of treatment (4 weeks)
b) greater frequency of hormone deficiency symptoms
c) increase in bleeding during the first few days →Gestagens irregular bleeding →Danazol a) high doses are required
b) long period of treatment (4–6 weeks)
c) side effects: acne, hirsutism and increase in weight

We claim:

1. Diagnostic treatment for improving the effectiveness of hysteroscopy, comprising administering an LH-RH antagonist and subsequently performing a hysteroscopy.

2. Treatment according to claim 1, wherein the LH-RH antagonist is cetrorelix.

3. Treatment according to claim 2, wherein, prior to hysteroscopy, cetrorelix is administered in a single dose of between 0.1 and 2 mg/kg of body weight.

4. Treatment according to claim 2, wherein, prior to hysteroscopy, cetrorelix is administered in a multiple dose of between 0.01 and 0,5 mg/kg of body weight.

5. Treatment according to claim 2, additionally comprising administering a treatment selected from the group consisting of endometriosis treatment, ablation of myomas or ablation of endometrial hyperplasia.

* * * * *